US009120878B2

(12) United States Patent
Lopez Villanueva et al.

(10) Patent No.: US 9,120,878 B2
(45) Date of Patent: Sep. 1, 2015

(54) METHOD FOR PRODUCING WATER-ABSORBENT POLYMER FOAMS

(75) Inventors: Francisco Javier Lopez Villanueva, Schifferstadt (DE); Markus Linsenbühler, Heidelberg (DE); Matthias Weismantel, Jossgrund-Oberndorf (DE); Bernd Siegel, Otterstadt (DE); Timo Baumgaertner, Monsheim (DE); Michael Fastner, Mannheim (DE)

(73) Assignee: BASF SE, Ludwigshafen (DE)

( * ) Notice: Subject to any disclaimer, the term of this patent is extended or adjusted under 35 U.S.C. 154(b) by 334 days.

(21) Appl. No.: 13/509,446

(22) PCT Filed: Nov. 19, 2010

(86) PCT No.: PCT/EP2010/067812
§ 371 (c)(1),
(2), (4) Date: May 11, 2012

(87) PCT Pub. No.: WO2011/061282
PCT Pub. Date: May 26, 2011

(65) Prior Publication Data
US 2012/0232176 A1    Sep. 13, 2012

(30) Foreign Application Priority Data

Nov. 23, 2009  (EP) ..................................... 09176761

(51) Int. Cl.
| C08J 9/00 | (2006.01) |
| C08L 33/08 | (2006.01) |
| C08F 2/10 | (2006.01) |
| A61L 15/42 | (2006.01) |
| A61L 15/60 | (2006.01) |
| C08F 2/18 | (2006.01) |
| C08F 2/48 | (2006.01) |
| C08J 9/30 | (2006.01) |
| C09J 133/02 | (2006.01) |
| C09J 133/06 | (2006.01) |

(52) U.S. Cl.
CPC . *C08F 2/10* (2013.01); *A61L 15/42* (2013.01); *A61L 15/60* (2013.01); *C08F 2/18* (2013.01); *C08F 2/48* (2013.01); *C08J 9/30* (2013.01); *C09J 133/02* (2013.01); *C09J 133/06* (2013.01); *C08J 2300/14* (2013.01); *C08J 2333/02* (2013.01)

(58) Field of Classification Search
CPC ........... A61L 15/42; A61L 15/60; C08F 2/10; C08F 2/18; C08F 2/48; C08J 9/30; C08J 2300/14; C08J 2333/02; C09J 133/02; C09J 133/06
USPC .............................. 521/69, 107, 113, 142, 149
See application file for complete search history.

(56) References Cited

U.S. PATENT DOCUMENTS

| 6,136,873 | A | 10/2000 | Hahnle et al. |
| 6,174,929 | B1 | 1/2001 | Hahnle et al. |
| 6,359,049 | B1 * | 3/2002 | Carrico et al. ................. 524/414 |
| 6,455,600 | B1 | 9/2002 | Hahnle et al. |
| 6,750,262 | B1 | 6/2004 | Hahnle et al. |
| 2005/0070616 | A1 | 3/2005 | Champ et al. |
| 2005/0249790 | A1 | 11/2005 | Weidl et al. |
| 2008/0161512 | A1 * | 7/2008 | Kawano et al. ............ 526/123.1 |
| 2009/0192035 | A1 | 7/2009 | Stueven et al. |

FOREIGN PATENT DOCUMENTS

| DE | 195 40 951 A1 | 5/1997 |
| WO | WO-97/17397 A1 | 5/1997 |
| WO | WO-97/31971 A1 | 9/1997 |
| WO | WO-99/44648 A1 | 9/1999 |
| WO | WO-00/52087 A1 | 9/2000 |
| WO | WO-03/057410 A1 | 7/2003 |
| WO | WO-03/066716 A1 | 8/2003 |
| WO | WO-2005/054356 A1 | 6/2005 |
| WO | WO-2006/109842 A1 | 10/2006 |

OTHER PUBLICATIONS

Buchholz, Fredric L., et al. *Modern Superabsorbent Polymer Technology*, "Solution Polymerization: Unit Operations and Their Effect on Product Quality." New York: John Wiley & Sons, Inc., 1998, pp. 71-103.
International Search Report in International Application No. PCT/EP2010/067812, dated Feb. 25, 2011.

* cited by examiner

*Primary Examiner* — Irina S Zemel
(74) *Attorney, Agent, or Firm* — Marshall, Gerstein & Borun LLP

(57) ABSTRACT

A process for preparing water-absorbing polymeric foams by polymerization of a foamed aqueous monomer solution or suspension, comprising an ethylenically unsaturated monomer which bears acid groups and may be at least partly neutralized, a crosslinker, a photoinitiator and a surfactant.

21 Claims, No Drawings

METHOD FOR PRODUCING WATER-ABSORBENT POLYMER FOAMS

CROSS-REFERENCE TO RELATED APPLICATIONS

This is the U.S. national phase of International Application No. PCT/EP2010/067812, filed Nov. 19, 2010, which claims the benefit of European Patent Application No. 09176761.6, filed Nov. 23, 2009.

The present invention relates to a process for preparing water-absorbing polymeric foams by polymerization of a foamed aqueous monomer solution or suspension comprising an ethylenically unsaturated monomer which bears acid groups and maybe at least partly neutralized, a crosslinker, a photoinitiator and a surfactant.

Being products which absorb aqueous solutions, water-absorbing polymers are used to produce diapers, tampons, sanitary napkins, panty liners, wound dressings and other hygiene articles, but also as water-retaining agents in market gardening. The water-absorbing polymers are also referred to as superabsorbents.

The production of water-absorbing polymers is described in the monograph "Modern Superabsorbent Polymer Technology", F. L. Buchholz and A. T. Graham, Wiley-VCH, 1998, pages 71 to 103.

Water-absorbing polymeric foams based on crosslinked monomers comprising acid groups are known, for example from EP 0 858 478 B1, WO 97/31971 A1, WO 99/44648 A1 and WO 00/52087 A1. They are produced, for example, by foaming a polymerizable aqueous mixture which comprises at least 50 mol % of neutralized, ethylenically unsaturated monomers comprising acid groups, crosslinker and at least one surfactant, and then polymerizing the foamed mixture. The polymerizable mixture can be foamed by dispersing fine bubbles of a gas which is inert toward free radicals, or by dissolving such a gas under elevated pressure in the polymerizable mixture and decompressing the mixture. The foams are used, for example, in hygiene articles for acquisition, distribution and storage of body fluids.

It was an object of the present invention to provide water-absorbing polymeric foams with an improved profile of properties, such as a high centrifuge retention capacity (CRC) and a low extractables content. In addition, the water-absorbing foams should comprise a low level of residual monomers and a low level of residual crosslinkers, and be very substantially white and not release any odors.

The object was achieved by a process for producing water-absorbing polymeric foams by polymerizing a foamed aqueous monomer solution or suspension comprising
  a) at least one ethylenically unsaturated monomer which bears acid groups and may be at least partly neutralized,
  b) at least one crosslinker,
  c) at least one photoinitiator and
  d) at least one surfactant,
  e) optionally one or more ethylenically unsaturated monomers copolymerizable with the monomers mentioned under a),
  f) optionally a solubilizer and
  g) optionally thickeners, foam stabilizers, polymerization regulators, fillers, fibers and/or cell nucleators,
the monomer solution or suspension being polymerized to a polymeric foam,
wherein the at least one photoinitiator is a compound of the general formula I

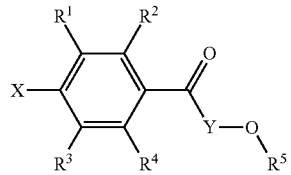

in which
  $R^1$, $R^2$, $R^3$, $R^4$ and $R^5$ are each independently hydrogen or $C_1$-$C_8$-alkyl, preferably each independently hydrogen or $C_1$-$C_4$-alkyl, more preferably each independently hydrogen or $C_1$-$C_2$-alkyl, where $C_3$-$C_8$-alkyl may be branched or unbranched,
  X is hydrogen, $OR^6$ or $C_1$-$C_8$-alkyl, preferably $OR^6$ or $C_1$-$C_4$-alkyl, more preferably $OR^6$ or $C_1$-$C_2$-alkyl, where $C_3$-$C_8$-alkyl may be branched or unbranched,
  $R^6$ is $C_1$-$C_8$-alkyl or $C_1$-$C_8$-hydroxyalkyl, preferably $C_1$-$C_4$-alkyl or $C_1$-$C_4$-hydroxyalkyl, more preferably $C_1$-$C_2$-alkyl or $C_1$-$C_2$-hydroxyalkyl, where $C_3$-$C_8$-alkyl or $C_3$-$C_8$-hydroxyalkyl may be branched or unbranched,
  Y is $C_4$-$C_8$-cycloalkyl, $C(R^7)R^8$ or $P(=O)R^7$
  $R^7$ and $R^8$ are each independently $C_1$-$C_8$-alkyl or $C_6$-$C_{12}$-aryl, preferably each independently $C_1$-$C_4$-alkyl or $C_6$-$C_{10}$-aryl, more preferably each independently $C_1$-$C_2$-alkyl or $C_6$-$C_8$-aryl, where $C_3$-$C_8$-alkyl or $C_9$-$C_{12}$-aryl may be branched or unbranched.

Very particular preference is given to photoinitiators c) of the general formula I in which $R^1$, $R^2$, $R^3$, $R^4$ and $R^5$ are each hydrogen, X is $OR^6$, $R^6$ is hydroxyethyl, Y is $C(R^7)R^8$, and $R^7$ and $R^8$ are each methyl (Irgacure® 2959), in which $R^1$, $R^2$, $R^3$, $R^4$ and $R^5$ are each hydrogen, X is hydrogen, Y is $C(R^7)$ $R^8$, and $R^7$ and $R^8$ are each methyl (Darocure® 1173), in which $R^1$, $R^2$, $R^3$, $R^4$ and $R^5$ are each hydrogen, X is hydrogen and Y is cyclohexyl (Irgacure® 184), and in which $R^1$ and $R^3$ are each hydrogen, $R^2$ and $R^4$ are each methyl, $R^5$ is ethyl, X is methyl, Y is $P(=O)R^7$, and $R^7$ is phenyl (Lucerin® TPO-L).

The amount of photoinitiator c) is preferably 0.001 to 2% by weight, more preferably 0.01 to 1% by weight, most preferably 0.05 to 0.2% by weight, based in each case on the unneutralized monomer a).

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, an acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The amount of monomer a) is preferably 20 to 90% by weight, more preferably 30 to 85% by weight, most preferably 35 to 75% by weight, based in each case on the unneutralized monomer a) and on the monomer solution or suspension. Based on the unneutralized monomer a) means in the context of this invention that the proportion of the monomer a) before the neutralization is used for the calculation, i.e. the contribution of the neutralization is not taken into account.

The acid groups of the monomers a) have typically been neutralized to an extent of 25 to 95 mol %, preferably to an extent of 40 to 85 mol %, more preferably to an extent of 50 to 80 mol %, especially preferably to an extent of 55 to 75 mol %, for which the customary neutralizing agents can be used, for example alkali metal hydroxides, alkali metal oxides, alkali metal carbonates or alkali metal hydrogencarbonates, and mixtures thereof. The neutralization can, however, also be undertaken with ammonia, amines or alkanolamines, such as ethanolamine, diethanolamine or triethanolamine.

In a preferred embodiment of the present invention, 10 to 90 mol %, preferably 20 to 80 mol %, more preferably 30 to 70 mol %, most preferably 40 to 60 mol %, of the neutralized monomers a) have been neutralized by means of an alkanolamine.

With a rising proportion of alkanolamine, both the flexibility of the polymeric foams and the extractables content increase.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.5 to 15% by weight, more preferably 2 to 10% by weight and most preferably 3 to 8% by weight, based in each case on the unneutralized monomer a). With rising crosslinker content, the centrifuge retention capacity (CRC) falls and the absorption under a pressure of 21.0 g/cm$^2$ (AUL 0.3 psi) passes through a maximum.

In addition to the photoinitiators c), the monomer solution or suspension may comprise further initiators. These initiators may be all compounds which generate free radicals under the polymerization conditions, for example thermal initiators, redox initiators.

Thermal initiators are, for example, peroxides, hydroperoxides, hydrogen peroxide, persulfates and azo initiators. Suitable azo initiators are, for example, 2,2'-azobis(2-amidinopropane)dihydrochloride, 2,2'-azobis(N,N-dimethylene)isobutyramidine dihydrochloride, 2-(carbamoylazo)isobutyronitrile, 2,2'-azobis[2-(2'-imidazolin-2-yl)-propane]dihydrochloride and 4,4'-azobis(4-cyanovaleric acid).

In a preferred embodiment of the present invention, combinations of photoinitiator c) and azo initiator are used. This allows particularly white water-absorbing polymeric foams with a particularly low level of residual monomers to be obtained.

The surfactants d) are of crucial significance for the preparation and the stabilization of the foamed monomer solution or suspension. It is possible to use anionic, cationic or nonionic surfactants or surfactant mixtures which are compatible with one another. It is possible to use low molecular weight or else polymeric surfactants, combinations of different types or else the same type of surfactants having been found to be advantageous. Usable nonionic surfactants are, for example, addition products of alkylene oxides, especially ethylene oxide, propylene oxide and/or butylene oxide, onto alcohols, amines, phenols, naphthols or carboxylic acids. The surfactants used are advantageously addition products of ethylene oxide and/or propylene oxide onto alcohols comprising at least 10 carbon atoms, where the addition products comprise 3 to 200 mol of ethylene oxide and/or propylene oxide added on per mole of alcohol. The addition products comprise the alkylene oxide units in the form of blocks or in random distribution. Examples of usable nonionic surfactants are the addition products of 7 mol of ethylene oxide onto 1 mol of tallow fat alcohol, reaction products of 9 mol of ethylene oxide with 1 mol of tallow fat alcohol, and addition products of 80 mol of ethylene oxide onto 1 mol of tallow fat alcohol.

Further usable commercial nonionic surfactants consist of reaction products of oxo alcohols or Ziegler alcohols with 5 to 12 mol of ethylene oxide per mole of alcohol, especially with 7 mol of ethylene oxide. Further usable commercial nonionic surfactants are obtained by ethoxylation of castor oil. For example, 12 to 80 mol of ethylene oxide are added on per mole of castor oil. Further usable commercial products are, for example, the reaction products of 18 mol of ethylene oxide with 1 mol of tallow fat alcohol, the addition products of 10 mol of ethylene oxide onto 1 mol of a $C_{13}/C_{15}$ oxo alcohol, or the reaction products of 7 to 8 mol of ethylene oxide onto 1 mol of a $C_{13}/C_{15}$ oxo alcohol. Further suitable nonionic surfactants are phenol alkoxylates, for example p-tert-butylphenol which has been reacted with 9 mol of ethylene oxide, or methyl ethers of reaction products of 1 mol of a $C_{12}$- to $C_{18}$-alcohol and 7.5 mol of ethylene oxide.

The above-described nonionic surfactants can be converted to the corresponding sulfuric monoesters, for example, by esterification with sulfuric acid. The sulfuric monoesters are used as anionic surfactants in the form of the alkali metal or ammonium salts. Suitable anionic surfactants are, for example, alkali metal or ammonium salts of sulfuric monoesters of addition products of ethylene oxide and/or propylene oxide onto fatty alcohols, alkali metal or ammonium salts of alkylbenzenesulfonic acid or of alkylphenol ether sulfates. Products of the type mentioned are commercially available. For example, the sodium salt of a sulfuric monoester of a $C_{13}/C_{15}$ oxo alcohol reacted with 106 mol of ethylene oxide, the triethanolamine salt of dodecylbenzenesulfonic acid, the sodium salt of alkylphenol ether sulfates and the sodium salt of the sulfuric monoester of a reaction product of 106 mol of ethylene oxide with 1 mol of tallow fat alcohol are commercial usable anionic surfactants. Further suitable anionic surfactants are sulfuric monoesters of $C_{13}/C_{15}$ oxo alcohols, paraffinsulfonic acids such as $C_{15}$ alkylsulfonate, alkyl-substituted benzenesulfonic acids and alkyl-substituted naphthalenesulfonic acids such as dodecylbenzenesulfonic acid and di-n-butylnaphthalenesulfonic acid, and also fatty alcohol phosphates such as $C_{15}/C_{18}$ fatty alcohol phosphate. The polymerizable aqueous mixture may comprise combinations of a nonionic surfactant and an anionic surfactant, or combinations of nonionic surfactants or combinations of anionic surfactants. Cationic surfactants are also suitable. Examples thereof are the dimethyl sulfate-quaternized reaction products of 6.5 mol of ethylene oxide with 1 mol of oleylamine, distearyldimethylammonium chloride, lauryltrimethylammonium chloride, cetylpyridinium bromide, and dimethyl sulfate-quaternized stearic acid triethanolamine ester, which is preferably used as a cationic surfactant.

The amount of surfactant, based on the unneutralized monomer a) is preferably 0.01 to 10% by weight, more preferably 0.1 to 6% by weight, most preferably 0.8 to 3% by weight.

Ethylenically unsaturated monomers e) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

Solubilizers f) are water-miscible organic solvents, for example dimethyl sulfoxide, dimethylformamide, N-methylpyrrolidone, monohydric alcohols, glycols, polyethylene glycols or monoethers derived therefrom, where the monoethers comprise no double bonds in the molecule. Suitable ethers are methylglycol, butylglycol, butyldiglycol, methyldiglycol, butyltriglycol, 3-ethoxy-1-propanol and glyceryl monomethyl ether.

If solubilizers f) are used, the content thereof in the monomer solution or suspension is preferably up to 50% by weight, more preferably 1 to 25% by weight, most preferably 5 to 10% by weight.

The monomer solution or suspension may comprise thickeners, foam stabilizers, fillers, fibers and/or cell nucleators g). Thickeners are used, for example, to optimize the foam structure and to improve the foam stability. This achieves the effect that the foam shrinks only slightly during the polymerization. Useful thickeners include all natural and synthetic polymers which are known for this purpose and increase the viscosity of an aqueous system significantly. These may be water-swellable or water-soluble synthetic and natural polymers. A detailed overview of thickeners can be found, for example, in the publications by R. Y. Lochhead and W. R. Fron, Cosmetics & Toiletries, 108, 95-135 (May 1993) and M. T. Clarke, "Rheological Additives" in D. Laba (ed.) "Rheological Properties of Cosmetics and Toiletries", Cosmetic Science and Technology Series, Vol. 13, Marcel Dekker Inc., New York 1993.

Water-swellable or water-soluble synthetic polymers useful as thickeners are, for example, high molecular weight polyethylene glycols or copolymers of ethylene glycol and propylene glycol, and high molecular weight polysaccharides such as starch, guar flour, carob flour, or derivatives of natural substances, such as carboxymethylcellulose, hydroxyethylcellulose, hydroxymethylcellulose, hydroxypropylcellulose and cellulose mixed ethers. A further group of thickeners is that of water-insoluble products such as fine silica, zeolites, bentonite, cellulose powder or other fine powders of crosslinked polymers. The monomer solution or suspension may comprise the thickeners in amounts up to 30% by weight. If such thickeners are used at all, they are present in the monomer solution or suspension in amounts of 0.1 to 10% by weight, preferably 0.5 to 20% by weight.

In order to optimize the foam structure, it is optionally possible to add hydrocarbons having at least 5 carbon atoms in the molecule to the aqueous reaction mixture. Suitable hydrocarbons are, for example, pentane, cyclopentane, hexane, cyclohexane, heptane, octane, isooctane, decane and dodecane. The useful aliphatic hydrocarbons may be straight-chain, branched or cyclic and have a boiling temperature above the temperature of the aqueous mixture during the foaming. The aliphatic hydrocarbons increase the shelf life of the as yet unpolymerized foamed aqueous reaction mixture. This eases the handling of the as yet unpolymerized foams and increases process reliability. The hydrocarbons act, for example, as cell nucleators and simultaneously stabilize the foam already formed. In addition, they can bring about further foaming in the course of polymerization of the monomer solution or suspension. They may then also have the function of a blowing agent. Instead of hydrocarbons or in a mixture therewith, it is optionally also possible to use chlorinated or fluorinated hydrocarbons as a cell nucleator and/or foam stabilizer, such as dichloromethane, trichloromethane, 1,2-dichloroethane, trichlorofluoromethane or 1,1,2-trichlorotrifluoroethane. If hydrocarbons are used, they are used, for example, in amounts of 0.1 to 20% by weight, preferably 0.1 to 10% by weight, based on the monomer solution or suspension.

In order to modify the properties of the foams, it is possible to add one or more fillers, for example chalk, talc, clay, titanium dioxide, magnesium oxide, aluminum oxide, precipitated silicas in hydrophilic or hydrophobic polymorphs, dolomite and/or calcium sulfate. The fillers may be present in the monomer solution or suspension in amounts of up to 30% by weight.

The above-described aqueous monomer solutions or suspensions are first foamed. It is possible, for example, to dissolve an inert gas, such as nitrogen, carbon dioxide or air, in the aqueous monomer solution or suspension under a pressure of, for example, 2 to 400 bar, and then to decompress it to standard pressure. In the course of decompression from at least one nozzle, a free-flowing monomer foam forms. Since gas solubility increases with falling temperature, the gas saturation and the subsequent foaming should be performed at minimum temperature, though undesired precipitations should be avoided. It is also possible to foam the aqueous monomer solutions or suspensions by another method, by dispersing fine bubbles of an inert gas therein. In the laboratory, the aqueous monomer solutions or suspensions can be foamed, for example, by foaming the aqueous monomer solution or suspension in a food processor equipped with egg beaters. In addition, it is possible to foam the aqueous monomer solutions or suspensions with carbon dioxide, by adding carbonates or hydrogencarbonates for neutralization.

The foam generation is preferably performed in an inert gas atmosphere and with inert gases, for example by admixing with nitrogen or noble gases under standard pressure or elevated pressure, for example up to 25 bar, and then decompressing. The consistency of the monomer foams, the size of the gas bubbles and the distribution of the gas bubbles in the monomer foam can be varied within a wide range, for example, through the selection of the surfactants d), solubilizers f), foam stabilizers, cell nucleators, thickeners and fillers g). This allows the density, the open-cell content and the wall thickness of the monomer foam to be adjusted easily. The aqueous monomer solution or suspension is preferably foamed at temperatures which are below the boiling point of the constituents thereof, for example at ambient temperature up to 100° C., preferably at 0 to 50° C., more preferably at 5 to 20° C. However, it is also possible to work at temperatures above the boiling point of the component with the lowest boiling point, by foaming the aqueous monomer solution or suspension in a vessel sealed pressure-tight. This gives monomer foams which are free-flowing and stable over a prolonged period. The density of the monomer foams is, at a temperature of 20° C., for example, 0.01 to 0.9 g/cm$^3$.

The resulting monomer foam can be polymerized on a suitable substrate. The polymerization is performed in the presence of the photoinitiators c). The free radicals can be generated, for example, by heating (thermal polymerization) or by irradiation with light of a suitable wavelength (UV polymerization).

Polymeric foams with a layer thickness of up to about 5 millimeters are produced, for example, by heating on one side or both sides, or more particularly by irradiating the monomer foams on one side or both sides. If relatively thick polymeric foams are to be produced, for example polymeric foams with thicknesses of several centimeters, heating of the monomer foam with the aid of microwaves is particularly advantageous, because relatively homogeneous heating can be achieved in this way. With increasing layer thickness, however, the proportion of unconverted monomer a) and crosslinker b) in the resulting polymeric foam increases. The thermal polymerization is effected, for example, at temperatures of 20 to 180° C., preferably in the range from 40° C. to 160° C., especially at temperatures from 65 to 140° C. In the case of relatively thick polymeric foams, the monomer foam can be heated and/or irradiated on both sides, for example with the aid of contact heating or by irradiation or in a drying cabinet. The resulting polymeric foams are open-cell. The proportion of open cells is, for example, at least 80%, preferably above 90%. Particular preference is given to polymeric foams with an open-cell content of 100%. The proportion of open cells in the polymeric foam is determined, for example, with the aid of scanning electron microscopy.

After the polymerization of the monomer foam or during the polymerization, the polymeric foam is dried. In the course of this, water and other volatile constituents are removed. Examples of suitable drying processes are thermal convection drying such as forced air drying, thermal contact drying such as roller drying, radiative drying such as infrared drying, dielectric drying such as microwave drying, and freeze drying.

The drying temperatures are typically in the range of 50 to 200° C., preferably 60 to 150° C., more preferably 80 to 120° C., most preferably 90 to 110° C. The preferred residence time at this temperature in the drier is preferably at least 1 minute, more preferably at least 2 minutes, most preferably at least 5 minutes, and typically at most 20 minutes.

In order to avoid undesired decomposition and crosslinking reactions, it may be advantageous to perform the drying under reduced pressure, under a protective gas atmosphere and/or under gentle thermal conditions, under which the product temperature does not exceed 120° C., preferably 100° C. A particularly suitable drying process is (vacuum) belt drying.

After the drying step, the polymeric foam usually comprises less than 15% by weight of water. The water content of the polymeric foam can, however, be adjusted as desired by moistening with water or water vapor.

To further improve the properties, the water-absorbing polymeric foams can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/31482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001 to 2% by weight, more preferably 0.02 to 1% by weight and most preferably 0.05 to 0.2% by weight, based in each case on the water-absorbing polymeric foam.

In a preferred embodiment of the present invention, polyvalent cations are applied to the water-absorbing polymeric foam in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate is preferred. Apart from metal salts, it is also possible to use polyamines as polyvalent cations.

The amount of polyvalent cation used is, for example, 0.001 to 1.5% by weight, preferably 0.005 to 1% by weight and more preferably 0.02 to 0.8% by weight, based in each case on the water-absorbing polymeric foam.

The surface postcrosslinking is typically performed in such a way that a solution of the surface postcrosslinker is sprayed onto the water-absorbing polymeric foams. After the spraying, the polymeric foams coated with the surface postcrosslinker are dried thermally, and the surface postcrosslinking reaction can take place either before or during the drying.

Preferred drying temperatures are in the range of 50 to 250° C., preferably 70 to 150° C., more preferably 850 to 120° C. and most preferably 90 to 110° C. The preferred residence time at this temperature in the drier is preferably at least 1 minute, more preferably at least 2 minutes, most preferably at least 5 minutes, and typically at most 20 minutes.

To improve the properties, the polymeric foams can additionally be coated or remoisturized.

Suitable coatings for improving the free swell rate (FSR) and the saline flow conductivity (SFC) are, for example, inorganic inert substances, such as water-insoluble metal salts, organic polymers, cationic polymers and di- or polyvalent metal cations, such as aluminum sulfate and aluminum lactate. Suitable coatings for counteracting the undesired caking tendency are, for example, fumed silica, such as Aerosil® 200, and surfactants, such as Span® 20. Suitable coatings for reducing the content of unconverted monomers (residual monomers) are, for example, reducing agents such as the salts of sulfurous acid, of hypophosphorous acid and/or of organic sulfinic acid. However, the reducing agent used is preferably a mixture of the sodium salt of 2-hydroxy-2-sulfinatoacetic acid, the disodium salt of 2-hydroxy-2-sulfonatoacetic acid and sodium hydrogensulfite. Such mixtures are available as Brüggolite® FF6 and Brüggolite® FF7 (Brüggemann Chemicals; Heilbronn; Germany).

By the process according to the invention, it is possible to produce water-absorbing polymeric foams with a high centrifuge retention capacity (CRC) and a low extractables content.

The present invention further provides the water-absorbing polymeric foams obtainable by the process according to the invention and water-absorbing polymeric foams with a centrifuge retention capacity (CRC) of at least 5 g/g and a residual monomer content of less than 0.15% by weight.

The water-absorbing polymeric foams according to the invention have a centrifuge retention capacity (CRC) of typically at least 5 g/g, preferably at least 6 g/g, more preferably at least 7 g/g, especially preferably at least 8 g/g, very especially preferably at least 9 g/g. The centrifuge retention capacity (CRC) of the water-absorbing polymeric foams is typically less than 20 g/g.

The inventive water-absorbing polymeric foams have a residual monomer content of typically less than 0.15% by weight, preferably less than 0.12% by weight, more preferably less than 0.1% by weight, especially preferably less than 0.075% by weight, most preferably less than 0.05% by weight.

The inventive water-absorbing polymeric foams have a residual crosslinker content of typically less than 0.002% by weight, preferably less than 0.001% by weight, more preferably less than 0.0005% by weight, especially preferably less than 0.0002% by weight, most preferably less than 0.0001% by weight.

The present invention further provides hygiene articles which comprise inventive water-absorbing polymeric foams. The hygiene articles are especially disposable diapers, tampons, sanitary napkins, panty liners and wound dressings.

Methods:

The measurements should, unless stated otherwise, be carried out at an ambient temperature of 23±2° C. and a relative air humidity of 50±10%. The water-absorbing polymer particles are mixed thoroughly before the measurement.

Residual Monomers

The residual monomers of the water-absorbing polymeric foam are determined analogously to the EDANA recommended test method No. WSP 210.2-05 "Residual Monomers".

Residual Crosslinkers

The residual crosslinker content of the water-absorbing polymeric foam polymer particle is determined by means of HPLC using a ZORBAX® Eclipse XDB C18 reverse-phase column (Agilent Technologies, US) with subsequent UV/VIS detection and calibration with an external standard. The mobile phase used is acetonitrile/water with a gradient.

Centrifuge Retention Capacity

The centrifuge retention capacity (CRC) of the water-absorbing polymeric foam is determined analogously to EDANA recommended test method No. WSP 241.2-05 "Centrifuge Retention Capacity".

Extractables Content

The extractables content of the water-absorbing polymeric foam is determined analogously to the EDANA recommended test method No. WSP 270.2-05 "Extractables", using the mean molar mass of the optionally partly neutralized monomer a) for the molar mass $M_{acr}$.

The EDANA test methods are obtainable, for example, from EDANA, Avenue Eugene Plasky 157, B-1030 Brussels, Belgium.

EXAMPLES

Example 1

209.1 g of acrylic acid, 81.3 g of a 37.3% by weight aqueous sodium acrylate solution, 16.8 g of Sartomer® SR-344 (diacrylate of a polyethylene glycol having a molar mass of approx. 400 g/mol), 25.6 g of a 15% by weight aqueous solution of Lutensol® AT80 (addition product of 80 mol of ethylene oxide onto 1 mol of a linear saturated $C_{16}$-$C_{18}$ fatty alcohol; BASF SE; Ludwigshafen; Germany) and 26.6 g of water were mixed in a beaker. Subsequently, 240.5 g of triethanolamine were added dropwise while cooling, in the course of which the temperature remained below 15° C.

The resulting homogeneous solution was transferred to a pressure vessel and saturated there with carbon dioxide at a pressure of 12 bar for 25 minutes. Under pressure, 8.0 g of a 3% by weight aqueous solution of Wako® V-50 (2,2'-azobis (2-amidinopropane)dihydrochloride) and 0.24 g of Irgacure® 2959 (1-[4-(2-hydroxyethoxy)phenyl]-2-hydroxy-2-methylpropan-1-one were added and admixed with a strong carbon dioxide stream. Subsequently, carbon dioxide was passed through the reaction mixture for a further 5 minutes. The carbon dioxide-saturated reaction mixture was then extruded at a pressure of 12 bar through a die with a diameter of 1.0 mm, which formed a fine-cell, free-flowing foam.

The base of a glass plate of DIN A3 size with edges of height 3 mm was covered with a transparent polyester film. The monomer foam obtained was applied to the glass plate and covered with a second transparent polyester film and a second glass plate. The foam sample was irradiated with UV light synchronously from both sides over 4 minutes, from above with a UVASPOT 1000/T UV/VIS radiator (Dr. Hönle A G; Gräfelfing; Germany), and from below with 2 UVASPOT 400/T UV/VIS radiators (Dr. Hönle A G; Gräfelfing; Germany). The distance of the upper lamp from the monomer foam was 39 cm and the distance of the lower lamps from the monomer foam was 13 cm.

The polymeric foam obtained was dried at 100° C. for 10 minutes in a forced-air drying cabinet and analyzed. The foam had a residual monomer content of 0.13% by weight, a residual crosslinker content of 0.0003% by weight, and a centrifuge retention capacity (CRC) of 8.4 g/g, and the extractables content was 55% by weight.

Example 2

Comparative Example

The procedure was as in example 1. The initiator used was 16.0 g of a 3% by weight aqueous solution of Wako® V-50 (2,2'-azobis-(2-amidinopropane)dihydrochloride). The foam had a residual monomer content of 0.72% by weight, a residual crosslinker content of 0.14% by weight and a centrifuge retention capacity (CRC) of 9.6 g/g, and the extractables content was 42% by weight.

Example 3

The procedure was as in example 1. The initiator used was 0.48 g of Irgacure® 2959 (1-[4-(2-hydroxyethoxy)phenyl]-2-hydroxy-2-methylpropan-1-one). The polymeric foam obtained was removable from the lower polyester film only with difficulty. The foam had a residual monomer content of 0.068% by weight, a residual crosslinker content of less than 0.0001% by weight and a centrifuge retention capacity (CRC) of 8.8 g/g, and the extractables content was 52% by weight.

Example 4

The procedure was as in example 1. The initiator used was 0.48 g of Lucirin® TPO-L (ethyl 2,4,6-trimethylbenzoylphenylphosphinate). The polymeric foam obtained was removable from the lower polyester film only with difficulty. The foam had a residual monomer content of 0.37% by weight, a residual crosslinker content of less than 0.0001% by weight and a centrifuge retention capacity (CRC) of 10.1 g/g, and the extractables content was 59% by weight.

Example 5

The procedure was as in example 1. The initiator used was 0.48 g of Irgacure® 184 (1-hydroxycyclohexyl phenyl ketone). The foam had a residual monomer content of 0.094% by weight, a residual crosslinker content of 0.0002% by weight and a centrifuge retention capacity (CRC) of 9.2 g/g, and the extractables content was 53% by weight.

Example 6

Comparative Example

The procedure was as in example 1. The initiator used was 0.48 g of Irgacure® 250 ((4-methylphenyl)[4-(2-methylpropyl)phenyl]iodonium hexafluorophosphate). The polymeric foam obtained has an unpleasant smell and was not removable from the polyester films. The foam had a residual monomer content of 1.6% by weight, a residual crosslinker content of 0.074% by weight and a centrifuge retention capacity (CRC) of 7.7 g/g, and the extractables content was 62% by weight.

Example 7

Comparative Example

The procedure was as in example 1. The initiator used was 0.48 g of 2-amino-9-fluorenone. The foam had a residual monomer content of 3.1% by weight, a residual crosslinker content of 1.1% by weight and a centrifuge retention capacity (CRC) of 8.8 g/g, and the extractables content was 80% by weight.

Example 8

The procedure was as in example 1. The initiator used was 0.48 g of Darocur® 1173 (2-hydroxy-2-methyl-1-phenylpropan-1-one). The foam had a residual monomer content of 0.045% by weight, a residual crosslinker content of less than 0.0001% by weight and a centrifuge retention capacity (CRC) of 9.0 g/g, and the extractables content was 63% by weight.

The invention claimed is:

1. A process for producing water-absorbing polymeric foams comprising providing an aqueous monomer solution or suspension comprising
  a) at least one ethylenically unsaturated monomer which bears an acid group and may be at least partly neutralized,
  b) at least one crosslinker,
  c) at least one photoinitiator, and
  d) at least one surfactant, and
  e) water;
foaming the aqueous monomer solution or suspension below boiling points of a) through e),
polymerizing the foamed monomer solution or suspension to a polymeric foam, wherein the at least one photoinitiator is a compound of the general formula I

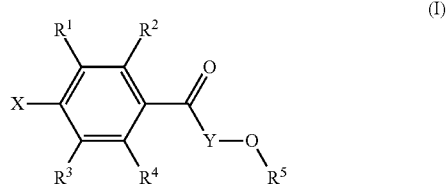

in which
  $R^1$, $R^2$, $R^3$, $R^4$, and $R^5$ are each independently hydrogen or $C_1$-$C_8$-alkyl, where $C_3$-$C_8$-alkyl may be branched or unbranched, X is hydrogen, OR$^6$, or C$_1$-C$_8$-alkyl, where C$_3$-C$_8$-alkyl may be branched or unbranched, R$^6$ is C$_1$-C$_8$-alkyl or C$_1$-C$_8$-hydroxyalkyl, where C$_3$-C$_8$-alkyl or C$_3$-C$_8$-hydroxyalkyl may be branched or unbranched, Y is C$_4$-C$_8$-cycloalkyl, C(R7)R8, or P(=O)R7

R$^7$ and R$^8$ are each independently C$_1$-C$_8$-alkyl or C$_6$-C$_{12}$-aryl, where C$_3$-C$_8$-alkyl or C$_9$-C$_{12}$-aryl may be branched or unbranched.

2. The process according to claim 1, wherein the at least one photoinitiator c) is a compound of the general formula I in which R$^1$, R$^2$, R$^3$, and R$^4$, and R$^5$ are each hydrogen, X is OR$^6$, R$^6$ is hydroxyethyl, Y is C(R$^7$)R$^8$, and R$^7$ and R$^8$ are each methyl.

3. The process according to claim 1, wherein the at least one photoinitiator c) is a compound of the general formula I in which R$^1$, R$^2$, R$^3$, R$^4$, and R$^5$ are each hydrogen, X is hydrogen, Y is C(R$^7$)R$^8$, and R$^7$ and R$^8$ are each methyl.

4. The process according to claim 1, wherein the at least one photoinitiator c) is a compound of the general formula I in which R$^1$ and R$^3$ are each hydrogen, R$^2$ and R$^4$ are each methyl, R$^5$ is ethyl, X is methyl, Y is P(=O)R$^7$, and R$^7$ is phenyl.

5. The process according to claim 1, wherein the at least one photoinitiator c) is a compound of the general formula I in which R$^1$, R$^2$, R$^3$, R$^4$, and R$^5$ are each hydrogen, X is hydrogen, and Y is cyclohexyl.

6. The process according to claim 1, wherein an azo initiator is additionally used.

7. The process according to claim 1, wherein the acid groups of the monomer a) have been neutralized to an extent of 25 to 95 mol %.

8. The process according to claim 1, wherein the neutralized acid groups of the monomer a) have been neutralized with an alkanolamine to an extent of 10 to 95 mol %.

9. The process according to claim 1, wherein the monomer solution or suspension, based on the unneutralized monomer a), comprises from 1 to 4% by weight of crosslinker b).

10. The process according to claim 1, wherein the monomer solution or suspension, based on the unneutralized monomer a), comprises from 0.05 to 0.2% by weight of photoinitiator c).

11. The process according to claim 1, wherein the monomer solution or suspension, based on the unneutralized monomer a) comprises from 0.05 to 0.1% by weight of surfactant d).

12. The process according to claim 1, wherein the monomer solution or suspension is foamed by dissolving an inert gas under pressure and subsequently decompressing.

13. A water-absorbing polymeric foam prepared by the process of claim 1.

14. The water-absorbing polymeric foam of claim 13 having a centrifuge retention capacity of at least 5 g/g and a residual monomer content of less than 0.15% by weight.

15. A hygiene article comprising a water-absorbing foam according to claim 13.

16. The process according to claim 1, wherein the polymeric foam has a residual monomer content of less than 0.15%, by weight.

17. The process according to claim 1, wherein the polymeric foam has a residual monomer content of less than 0.05%, by weight.

18. The process according to claim 1, wherein the polymeric foam has a residual crosslinker content of less than 0.001%, by weight.

19. The process according to claim 1, wherein the polymeric foam has a residual crosslinker content of less than 0.0005%, by weight.

20. The process according to claim 1, wherein the aqueous monomer solution or suspension is foamed at 0 to 50° C.

21. The process according to claim 1, wherein the aqueous monomer solution or suspension is foamed at 5 to 20° C.

* * * * *